United States Patent
Tschirren et al.

(10) Patent No.: US 10,441,729 B2
(45) Date of Patent: Oct. 15, 2019

(54) AUTOINJECTOR WITH SELECTABLE RELEASE MODE

(71) Applicant: TecPharma Licensing AG, Burgdorf (CH)

(72) Inventors: Markus Tschirren, Burgdorf (CH); Jürg Hirschel, Bern (CH); Marc Fiechter, Konolfingen (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 15/255,635

(22) Filed: Sep. 2, 2016

(65) Prior Publication Data

US 2016/0367763 A1 Dec. 22, 2016

Related U.S. Application Data

(63) Continuation of application No. PCT/CH2015/000028, filed on Feb. 24, 2015.

(30) Foreign Application Priority Data

Mar. 6, 2014 (CH) .......................... 333/14

(51) Int. Cl.
*A61M 5/32* (2006.01)
*A61M 5/20* (2006.01)
*A61M 5/315* (2006.01)

(52) U.S. Cl.
CPC ........ *A61M 5/3257* (2013.01); *A61M 5/2033* (2013.01); *A61M 5/3157* (2013.01);
(Continued)

(58) Field of Classification Search
CPC .......... A61M 5/2033; A61M 2205/581; A61M 2005/2013; A61M 2005/2073;
(Continued)

(56) References Cited

U.S. PATENT DOCUMENTS

2005/0101919 A1 5/2005 Brunnberg
2011/0213314 A1 9/2011 Guillermo
(Continued)

FOREIGN PATENT DOCUMENTS

AU 2010269142 B2 8/2012
CH 705992 A2 6/2013
(Continued)

OTHER PUBLICATIONS

PCT Search Report dated May 6, 2015 for International Application No. PCT/CH2015/000028 (filed Feb. 24, 2015), 2 pages.
(Continued)

*Primary Examiner* — Emily L Schmidt
(74) *Attorney, Agent, or Firm* — Dorsey & Whitney LLP (57) ABSTRACT

An injection device for administering a liquid medicament includes a generally elongate housing, a syringe holder in which a syringe can be placed, said syringe containing a medication, a stop and a needle on the distal area thereof, a needle protection housing which is arranged so it can be moved axially on the housing and which protrudes at a certain distance from the distal end of the housing.

21 Claims, 9 Drawing Sheets

(52) U.S. Cl.
CPC ...... *A61M 5/3158* (2013.01); *A61M 5/31505* (2013.01); *A61M 5/326* (2013.01); *A61M 2005/206* (2013.01); *A61M 2005/208* (2013.01); *A61M 2005/2013* (2013.01); *A61M 2005/2026* (2013.01); *A61M 2005/2073* (2013.01); *A61M 2205/581* (2013.01); *A61M 2205/582* (2013.01)

(58) Field of Classification Search
CPC .............. A61M 5/3157; A61M 5/3158; A61M 5/31501; A61M 5/3257
See application file for complete search history.

(56) References Cited

U.S. PATENT DOCUMENTS

| | | | | |
|---|---|---|---|---|
| 2012/0123350 | A1* | 5/2012 | Giambattista | A61M 5/2033 604/198 |
| 2012/0310156 | A1* | 12/2012 | Karlsson | A61M 5/2066 604/89 |

FOREIGN PATENT DOCUMENTS

| | | | |
|---|---|---|---|
| EP | 1349590 | B1 | 5/2006 |
| WO | 2009040602 | A1 | 4/2009 |
| WO | 2011005177 | A1 | 1/2011 |

OTHER PUBLICATIONS

PCT International Preliminary Report on Patentability dated Sep. 6, 2016 for for International Application No. PCT/CH2015/000028 (filed Feb. 24, 2015), 14 pages.

\* cited by examiner

AUTOINJECTOR WITH SELECTABLE RELEASE MODE

CROSS-REFERENCE TO RELATED APPLICATIONS

This application is a Continuation of International Patent Application No. PCT/CH2015/000028 filed Feb. 24, 2015, which claims priority to Swiss Patent Application No. 333/14 filed Mar. 6, 2014. The entire contents of each are incorporated herein by reference for any and all purposes.

BACKGROUND

The invention is in the field of the injection devices for administering a liquid product, in particular a medicament. The invention relates to an injection device according to the preamble of Claim 1.

The term "medicament" here covers any free-flowing medicinal formulation that is suitable for controlled administration through a means such as, for example, a cannula or a hollow needle, comprising, for example, a liquid, a solution, a gel or a fine suspension containing one or more medicinal active substances. A medicament can be a composition with a single active ingredient or a premixed or co-formulated composition with several active ingredients from a single container. Medicaments include drugs such as peptides (for example, insulin, insulin containing medicaments, GLP-1 containing as well as derived or analogous preparations), proteins and hormones, biologically obtained or biologically active ingredients, active ingredients based on hormones or genes, nutrient formulations, enzymes, vaccines, DNA or RNA or oligonucleotides, antibodies or parts of antibodies as well as suitable base, auxiliary and carrier substances.

From the prior art, injection devices are known that have functions such as automatic insertion and release. Such an injection device is known from EP1349590 or US2005/0101919. These documents describe an injection device that comprises, for releasing, that is to say for starting the automatic insertion and release movement of the injection device, a release device in the form of a button in the proximal area of the injection device. Furthermore, they disclose a needle protection sleeve, which is pressed on an injection site, in order to shift the needle protection sleeve from a distal into a proximal position. The injection can only be released if the needle protection sleeve is pushed on the injection site, and the needle protection sleeve is in its proximal position and if the button was actuated subsequently. In this injection device, the button cannot be pushed before the needle protection sleeve is not in its proximal position.

SUMMARY

The problem of the invention is to provide an improved injection device by means of which a safe release is possible.

The problem is solved by the characterizing features of Claim 1. Advantageous developments result from the dependent claims.

The invention relates to an injection device for administering a liquid medicament. The injection device comprises a generally elongate housing, a syringe holder wherein a syringe can be placed and wherein the syringe contains a medicament and a plug and comprises a needle in its distal area, a needle protection sleeve, which is placed axially movably on the housing and which protrudes at a certain distance from the distal end of the housing. A drive device, which comprises a piston rod and a loaded drive spring and which is coupled to a holding device and held in a stressed state by means of a release device, and which, after the release, first acts on the syringe in order to shift it in the distal direction and then acts on the plug in order to inject the medicament from the syringe, a release button assembly, which has a release button, in order to uncouple the drive device from the holding device, wherein the release button assembly is designed so that it has a site of connection to the piston rod, so that a distally directed movement of the release button assembly moves the piston rod in the distal direction from a first position into a second position, and, via the connection of the holding device to the drive device, the holding device can also be moved in the distal direction. When the release button is pushed and moved from its proximal position into a distal position, then, in particular, the piston rod can be shifted as a result together with the holding device in the distal direction from the first position into the second position.

The release device comprises a releasing element and is axially movable in the housing and connected to the needle protection sleeve. When the needle protection sleeve is placed on the skin of the patient, the needle protection sleeve is moved in the proximal direction, and the resulting effect is that the release device also moves in the proximal direction.

The drive device is placed in the holding device and detachably engaged to the holding device and to the releasing element.

For releasing the injection device, the drive device must be uncoupled from the holding device, so that the driving device first moves the syringe in the distal direction in order to insert the needle, and then the piston is moved in the distal direction for the release of the medicament.

The drive device can be released by means of two releasing modes.

The patient himself/herself can select which of the two releasing modes he/she prefers.

In a first releasing mode, the patient first pushes the release button from the proximal position into the distal position and then places the injection device on the skin, in order to move the needle protection sleeve in the proximal direction and thus start the injection.

In the second releasing mode, the patient first pushes the injection device on the skin, and the needle protection sleeve is moved in the distal direction and thus positions the pen on the skin, and, when ready, the patient pushes the release button from the proximal position into the distal position, in order to release the injection.

In both cases, a sequential shifting of the needle protection sleeve in the proximal direction and a shifting of the release button in the distal direction are needed.

The two releasing modes have the following two movement courses and can occur in different sequences in order to start the injection. In the first movement course, by pushing of the release button, the release button and the piston rod in connection with the holding device, which is coupled to the piston rod, are shifted in the distal direction. In the second movement course, the needle protection sleeve in connection with the releasing element is shifted in the proximal direction. The two movement courses have the effect that the holding device is shifted by a defined distance in relation to the releasing element, and, in this way, the holding device can be released from the releasing element, in order to uncouple the driving element from the holding device and release the injection.

BRIEF DESCRIPTION OF THE DRAWINGS

FIGS. 2 and 3 are cross-sectional representations of an injection device according to the invention with a cap in place in the delivery state, wherein FIG. 2 is a view that has been rotated with respect to FIG. 3 by 90° about the longitudinal axis.

FIGS. 4 and 5 are cross-sectional representations of an injection device according to the invention, wherein the injection device is shown placed on the injection site, and wherein FIG. 4 is a view that has been rotated with respect to FIG. 5 by 90° about the longitudinal axis.

FIGS. 6 and 7 are cross-sectional representations of an injection device according to the invention, wherein the release button has been pushed from a proximal position into a distal position, and wherein FIG. 6 is a view that has been rotated with respect to FIG. 7 by 90° about the longitudinal axis.

FIGS. 8 and 9 are cross-sectional representations of an injection device according to the invention, wherein the needle protection sleeve has been shifted in the proximal direction and the release button in the distal direction, and thus the injection device is shown in the released state, and wherein FIG. 8 is a view that has been rotated with respect to FIG. 9 by 90° about the longitudinal axis.

FIGS. 10 and 11 are cross-sectional representations of an injection device according to the invention, wherein the content of the medicament has been released, and the signaling device has generated a final click, and wherein FIG. 10 is a view that has been rotated with respect to FIG. 11 by 90° about the longitudinal axis.

FIGS. 12 and 13 are cross-sectional representations of an injection device according to the invention, wherein the injection device has been removed from the injection site, and the final locking of the needle protection sleeve has taken place, and wherein FIG. 12 is a view that has been rotated with respective to FIG. 13 by 90° about the longitudinal axis.

FIGS. 14 and 15 are cross-sectional representations of an injection device according to the invention with another embodiment of the release button assembly, wherein FIG. 14 is a view that has been rotated with respect to FIG. 15 by 90° about the longitudinal axis.

FIGS. 16 and 17 are cross-sectional representation of an additional injection device according to the invention with another embodiment of the release button assembly, wherein FIG. 16 is a view that has been rotated with respect to FIG. 17 by 90° about the longitudinal axis.

DETAILED DESCRIPTION

Unless otherwise indicated, identical reference numerals refer to identical parts.

Figure 1:
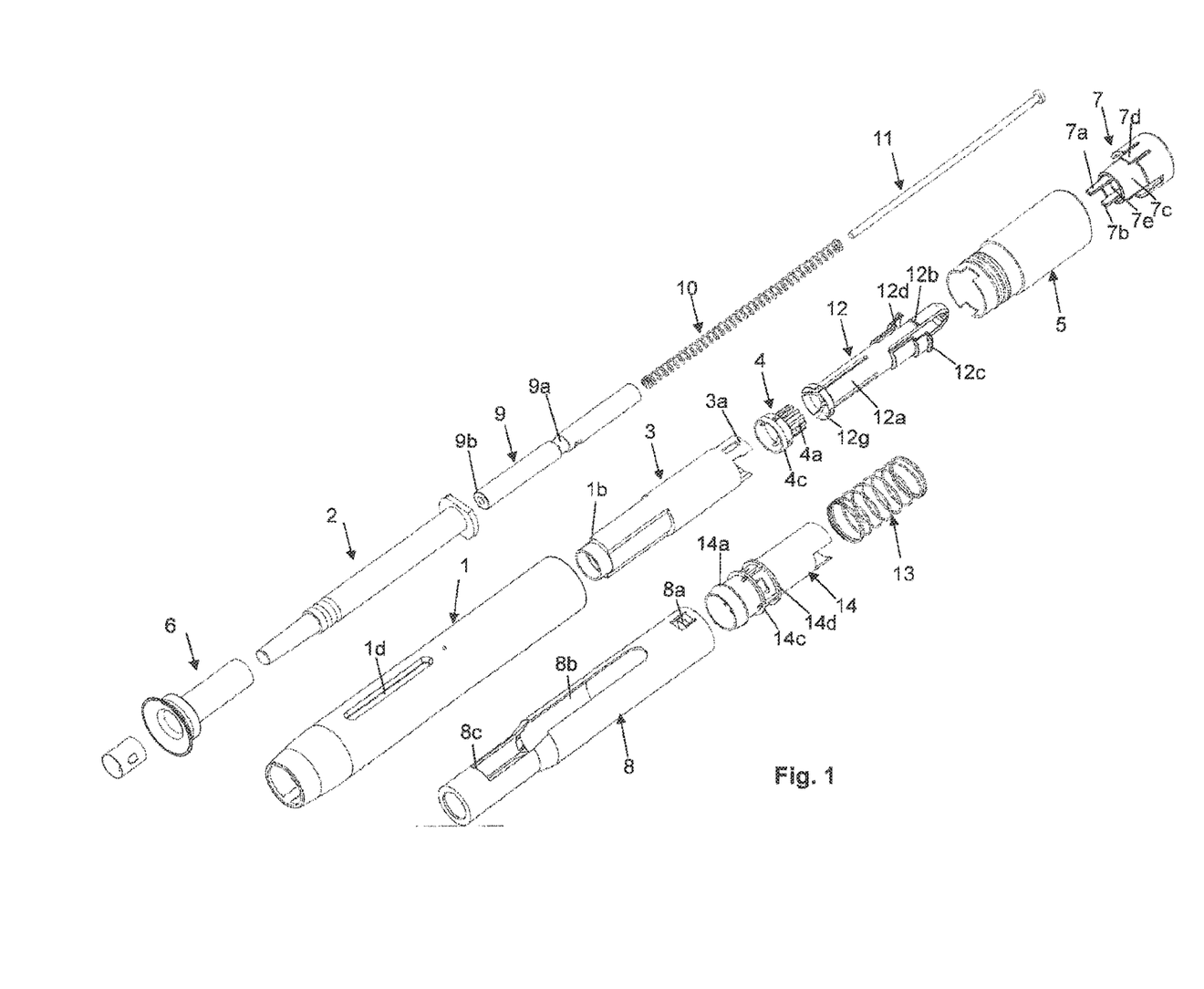
FIG. 1 is an exploded view of an injection device according to the invention.
Figure 2:
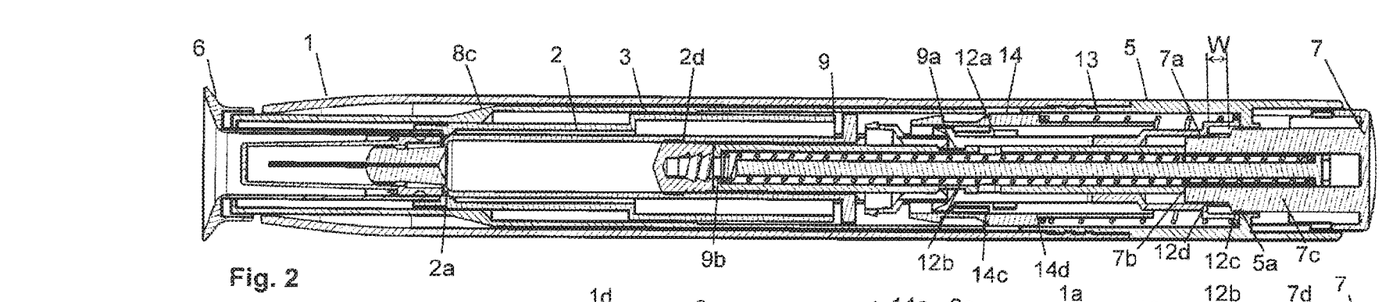
Figure 3:
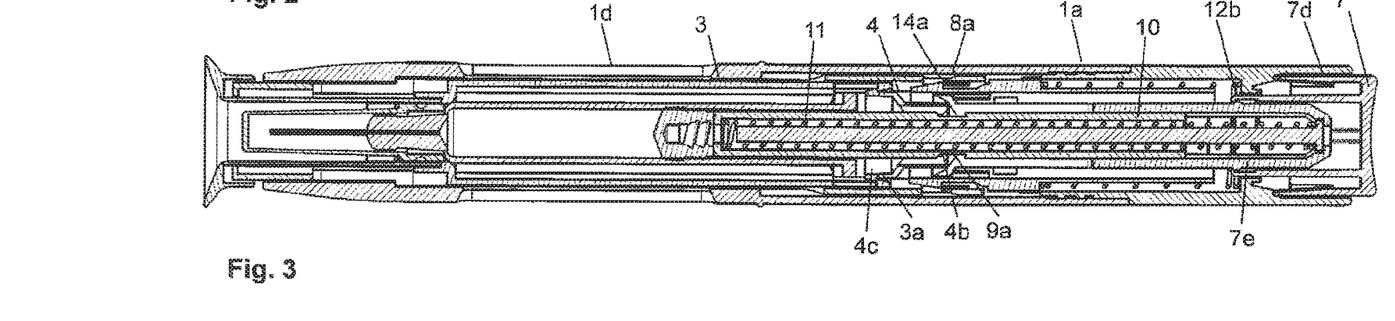

The injection device, for example, an autoinjector as shown in FIGS. 1, 2 and 3, comprises a housing with a distal housing portion 1 and a proximal housing portion 5 with a cap 6 in place in the delivery state. The distal housing portion 1 and the proximal housing portion 5 are connected to one another by latching connections or thread connection.

In the distal housing portion 1, a product container 2 is accommodated, on the distal end of which an injection needle for the release of a liquid product contained in the product container 2 is located. On the proximal end, the product container 2 has a shiftable piston 2d, whose movement in relation to the product container 2 and in the direction of the injection needle produces a product release, wherefore one can also speak of a release movement.

The injection device moreover comprises a needle protection sleeve 8, wherein the needle protection sleeve 8 has a distal area with a first diameter, and a proximal area with a larger diameter. In FIG. 1, at least one window 8b on the needle protection sleeve 8 can be seen, as a result of which the product container 2 (e.g., syringe) is also visible in the built-in state. On the inner side of the needle protection sleeve 8, an injection step 8c is provided. On the proximal end of the needle protection sleeve 8, two recesses are provided, which comprise inward directed needle protection abutments 8a. The needle protection sleeve 8 is placed in a manner so it can be shifted axially in the housing, and the distal area of the needle protection sleeve 8 protrudes from the distal end of the distal housing portion 1. The needle protection sleeve 8 is attached by means of the needle protection sleeve abutment 8a and via rib abutments 14a on a releasing element 14, and secured against further distal movement and via the window 8b against twisting. For this purpose, a frame ledge of the window 1d protrudes radially inward into the window opening 8b.

The device moreover comprises a syringe holder 3, which is placed axially movable in the needle protection sleeve 8, wherein the syringe holder 3 has a shoulder support 2a for the product container 2 (e.g., prefilled syringe), and the product container 2 is positioned in the syringe holder 3 above the shoulder support 2a. The syringe holder 3 is coupled by means of proximally directed arms 3a with inward facing protrusions 3b to the insertion sleeve 4. The insertion sleeve 4 is configured in the shape of a ring, and, in its distal area, it has an annular shoulder 4c, to which the syringe holder 3 is hooked with its proximally directed arms 3a. Moreover, the insertion sleeve 4 has proximally flexible arms 4a with an inward directed hook 4b, which in turn is snapped into the groove 9a of the piston rod 9.

Furthermore, the device comprises the releasing element 14, which is placed axially movable in the housing and connected to the needle protection sleeve 8 (as already described herein). The releasing element 14 is configured in the shape of a sleeve and conical at the distal end, and, at the distal outer periphery, it has the rib abutment 14a. At a small distance from the rib abutment 14a, a first ring 14c is placed on the outer periphery, and a second ring 14d is placed at a greater distance from the rib abutment 14a. On the inner side, the releasing element 14 comprises blocking means 14b.

The injection device moreover comprises a holding device 12, which is placed axially movable in the releasing element 14. The holding device 12 comprises spring arms 12a, which, in their distal area, comprise inward projecting protuberances 12g. Furthermore, the holding device 12 comprises proximally directed wings which, in the proximal area, comprise a needle protection spring supporting surface 12c and, slightly distally therefrom and on the inner side of the wings, a gradation 12d.

The injection device also comprises a drive device, which is placed axially in the holding device 12 and which is detachably engaged to the holding device 12 and to the releasing element 14. The drive device is controlled via the holding device 12 and via the releasing element 14 (as explained in further detail herein). The drive device is configured to store drive energy and to move the syringe holder 3 in the distal direction in a first step and then release the contents of the syringe 2, and, after the completion of the release, move the holding device 12 in the proximal direction, in order to generate an acoustic and/or tactile signal and signal the end of the injection to the user.

The drive device comprises a piston rod 9, which acts on the plug 2d, and a drive spring 10, which is loaded, in order to move the piston rod 9 and drive the syringe holder 3 in the distal direction in a first step for inserting the needle, and in order to move the plug 2d in the distal direction, in an additional step, for the release of the medicament. The piston rod 9 is placed axially movable in the holding device 12, and the drive spring 10 is attached in the piston rod 9 between a distal wall 9b of the piston rod 9 and a proximal end of the holding device 12. In addition, a guiding pin 11 may be positioned within the drive spring 10.

The piston rod 9 has a peripheral groove 9a on its peripheral sheath. The groove is designed so that the protuberances 12g of the spring arms 12a of the holding device 12, and the hooks 4b of the flexible arms 4a of the insertion sleeve 4 can engage in the groove 9a.

Moreover, the injection device comprises a needle protection spring 13, which is distally in contact with the second ring 14d of the releasing element 14 and proximally with the holding device 12 on the needle protection spring supporting surface 12c.

Furthermore, the device comprises a release button 7. The release button is retained by means of spring arms 7d in the proximal area and by means of a peripheral groove 7e on a rib catch 12b of the holding device 12 in its proximal direction. The release button 7 has a button sheath 7c and, in the distal area of the button sheath 7c, on the inner side, the peripheral groove 7e is provided, into which the rib catch 12b can engage. Moreover, extension arms 7a extending in the distal direction, which have a supporting surface 7b in the distal area, are formed on the release button 7.

In the assembled state, the two housing portions are firmly connected. In the unused state, the piston rod 9 is held with the drive spring 10 in the stressed state. By means of the inward protruding spring arms 12a of the holding device 12, which detachably engage from a locking connection in the peripheral groove 9a of the piston rod 9, and by the sleeve-shaped releasing element 14, which surround the spring arms 12a and thus prevent the opening of the arms 12a, the drive spring 10 is held in the stressed state. In addition, the insertion sleeve 4 also engages by means of the hooks 4b of the flexible arms 4a in the peripheral groove 9a of the piston rod 9. The syringe 2, the syringe holder 3, and the needle protection sleeve 8 are attached in the distal housing portion 1, so that a portion of the needle protection sleeve 8 protrudes out of the distal end of the distal housing portion 1. Proximally directed arms 3a with inward facing protrusions 3b on the syringe holder 3 engage in the peripheral annular shoulder 4c on the insertion sleeve 4. At the same time, the proximal area of the needle protection sleeve 8 is located in front of the first ring 14c of the releasing element 14, whereby proximal movements of the needle protection sleeve 8 can be transmitted to the releasing element 14, and distal movements of the releasing element 14 can be transmitted to the needle protection sleeve 8. The releasing element 14 is applied with the distal abutment of the blocking means 14b against the distal area of the spring arms 12a. The extension arms 7a of the release button 7 are placed with their distal supporting surface 7b on the proximal area of the piston rod 9, so that the end area of the button sheath 7c is at a defined distance W from the gradation 12d of the holding device 12 (see FIG. 2). The spring arms 7d of the release button 7 are applied against an inclined surface in the interior of the proximal housing portion 5 and form a drive surface with the housing for a resetting of the release button 7.

The releasing element 14 and the release button 7 are arranged so that they can interact with one another independently of the sequence in which they are actuated and release the injection apparatus.

Figure 4:
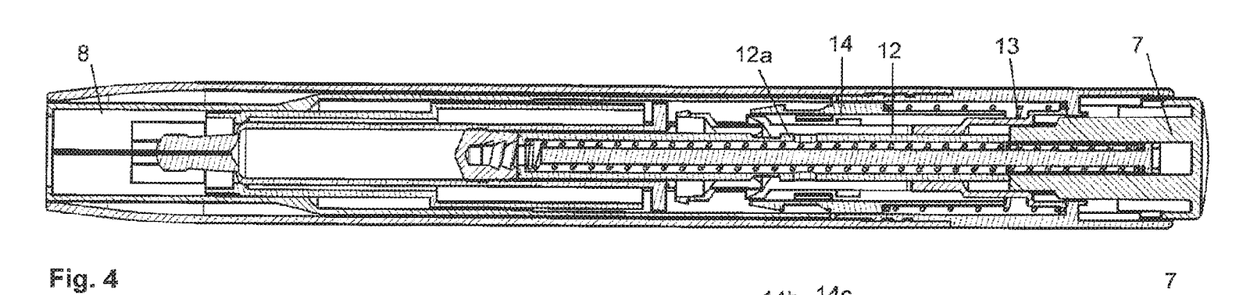
Figure 5:
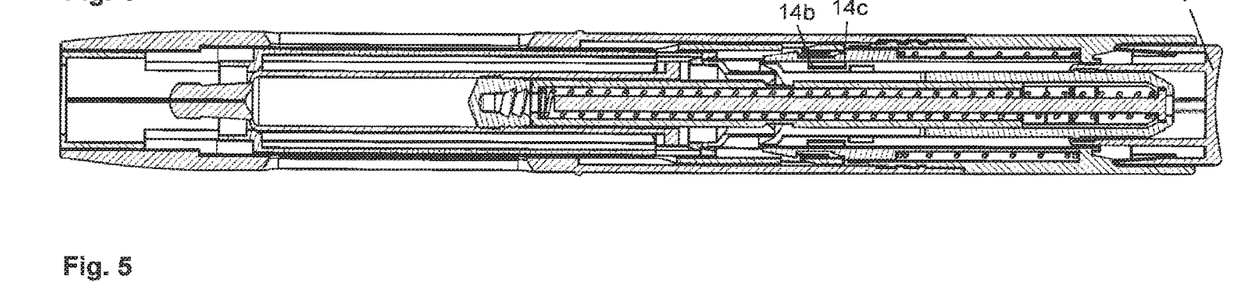

FIGS. 4 and 5:

The releasing element 14 is actuated first, and the release button 7 is actuated second. When, first, the distal area of the needle protection sleeve 8 is shifted against the force of the needle protection spring 13 in the proximal direction into the housing, the proximal end of the needle protection sleeve 8 comes in contact with the first ring 14c of the release ring element 14, and its movement also moves the releasing element 14 in the proximal direction, and the protuberances 12g of the flexible spring arms 12a of the holding device 12 reach the distal end of the releasing element 14. If, before pushing the release button 7, the user removes the injection device from the injection site and thus interrupts the release of the injection apparatus, the loaded needle protection spring 13 moves the releasing element 14 and thus also the needle protection sleeve 8 back into its start position.

Figure 6:
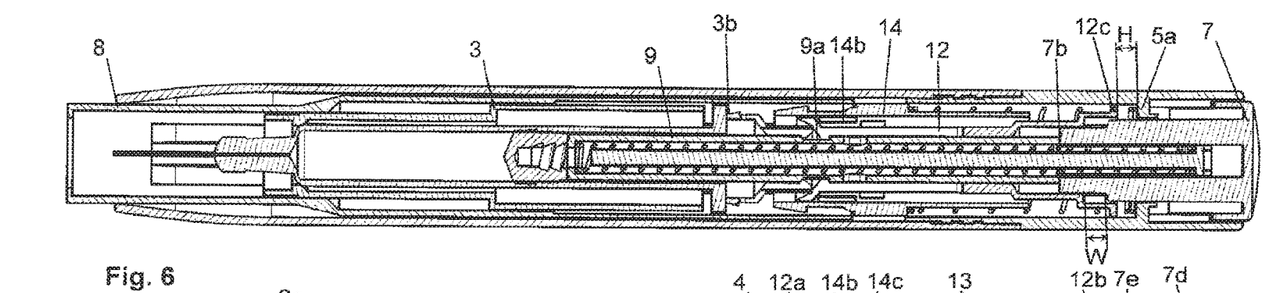
Figure 7:
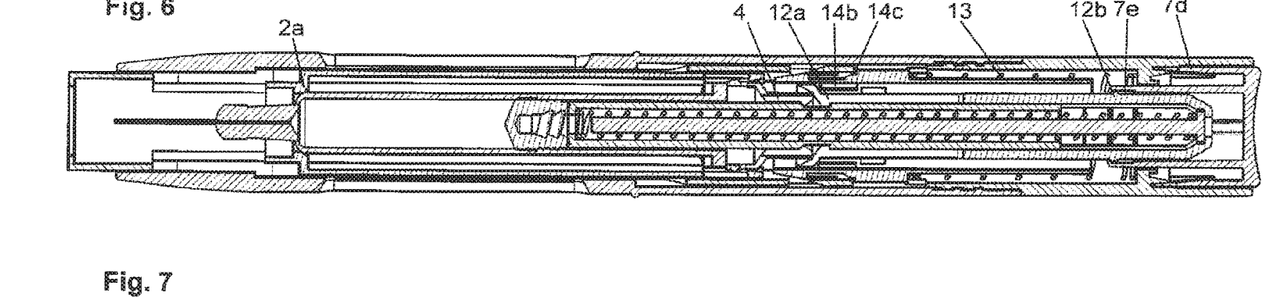

FIGS. 6 and 7:

The release button 7 is activated first, and the release element 14 is actuated second.

When the release button 7 is pushed from its proximal position into a distal position, then the extension arms 7a with their supporting surfaces 7b reach the proximal area of the piston rod 9, and thus the piston rod 9 and also the holding device 12, which is coupled to the piston rod, are also shifted in the distal direction from a first position into a second position. As already described in FIGS. 4 and 5, the flexible spring arms 12a of the holding device 12 reach the distal end of the releasing element 14. In the same way, the proximal area of the needle protection spring supporting surface 12c is moved in the distal direction by a button stroke H from the intermediate bottom 5a. Due to the axial shifting of the release button 7 and the simultaneous shifting or driving of the holding device 12 by means of the piston rod 9, due to the engagement of the spring arms 12a in the groove 9a, the distance H remains between the gradation 12d and the distal area of the button sheath 7c, when the release button 7 is pushed. Furthermore, the flexible arms 7d of the release button 7 are bent radially inward on the inclined surface of the housing and stressed. Moreover, during the distal movement of the holding device 12, pressure is exerted on the needle protection spring 13, which is stressed between the needle protection spring supporting surface 12c and the releasing element 14, as a result of which the releasing element 14, and, over the first ring 14c, the needle protection sleeve 8 as well are moved in the distal direction. The releasing element 14 is moved in the distal direction until the blocking means 14b is again in the distal area of the spring arms 12a. If, in this case too, the user interrupts the release of the injection apparatus and takes the pressure off the release button 7, before pushing the needle protection sleeve 8 on the injection site, the spring arms 7d of the release button 7, which are stressed on the inclined housing surface, become unstressed, and the release button 7 as a result moves in the proximal direction, wherein the needle protection spring 13 also becomes unstressed and thus the holding device 12 is also pushed into its start position. The holding device 12 is shifted in the proximal direction to the distal abutment of the abutment element 14b of the releasing element 14.

Figure 8:
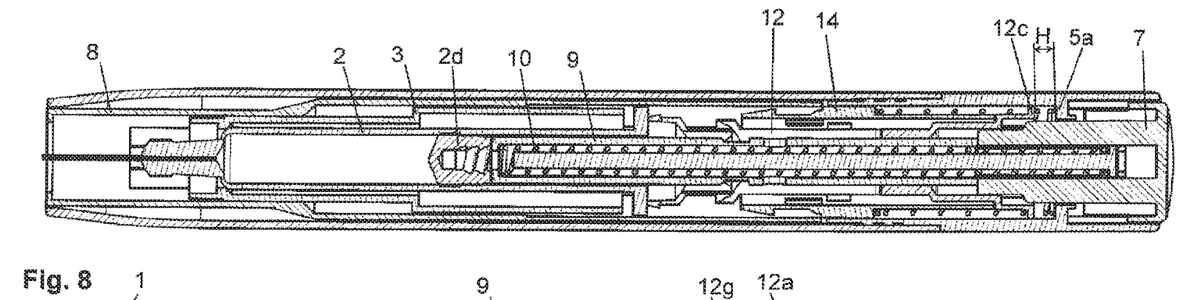
Figure 9:
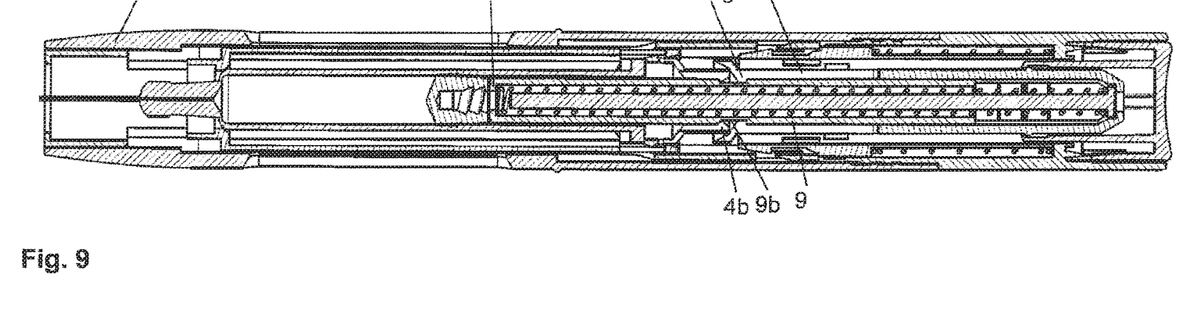

FIGS. 8 and 9:

If the release button 7 is then pushed in the distal direction, before or after the needle protection sleeve 8 has been pushed on the injection site and shifted in the proximal direction, these two movement courses have the effect that the holding device 12 is shifted in relation to the releasing element 14 by a defined distance, in particular until the distal area of the spring arms 12a of the holding device 12 comes out of the distal area of the release element 14, and, as a result, the spring arms 12a can open radially and release the protuberances 12g from the peripheral groove 9a of the piston rod 9, wherein the piston rod 9 is released and can be moved by the stressed drive spring 10 in the distal direction. In the process, the distally inclined outer surfaces of the spring arms 12a engage over the distal margin of the releasing element 14, whereby the holding device 12 is held in position, and thus the proximal side of the needle protection spring supporting surface 12c is also kept at a distance equivalent to the button stroke H away from the intermediate bottom 5a of the housing.

During the distal movement of the piston rod 9, the proximally directed flexible arms 4a of the insertion sleeve 4 open, and the inward directed hooks 4b can be released from the peripheral groove 9a of the piston rod. This occurs since the flexible arms 4a are no longer held by the distal area of the spring arms 12a of the holding device, since, due to their radial movement, the spring arms 12a are in an outwardly open state.

Figure 10:
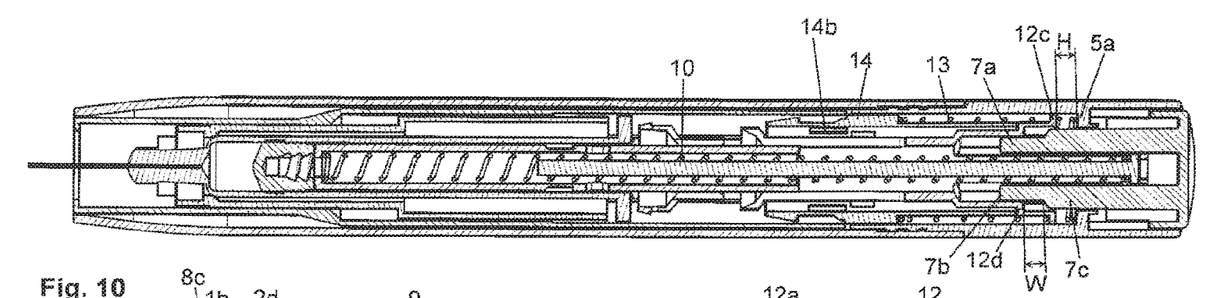
Figure 11:
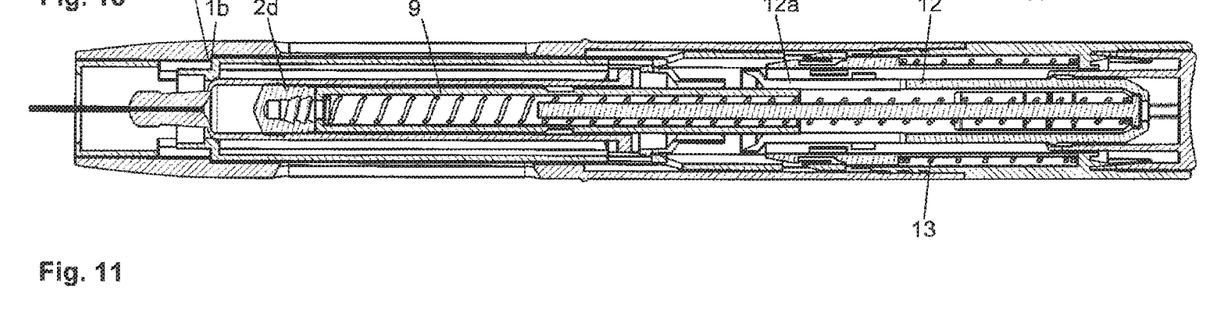

FIGS. 10 and 11:

The force of the drive spring 10 drives the piston rod 9 in order to move the plug 2d of the syringe 2 in the distal direction. By means of the drive force of the drive spring 10 onto the plug 2d and the friction force of the plug 2d with the syringe 2, the syringe 2 with the syringe holder 3 first of all moves in the distal direction and the needle is inserted in the injection site. The insertion process is terminated via the needle protection sleeve 8 when the syringe holder 3 with an offset lb is applied on the insertion ledge 8c provided in the distal area of the needle protection sleeve 8. As a result, the force of the drive spring 10 acts on the plug 2d and drives said plug into the syringe 2 in order to release the medicament. After the medicament has been released and the proximal end of the piston rod 9 has passed the distal end of the spring arms 12a of the holding device 12, the spring arms 12a can move radially inward and be released from the releasing element 14. Since the force of the drive spring 10 acts proximally onto the holding device 12, and since this holding device is no longer held via the releasing element 14, the holding device 12 is guided axially by the releasing element 14 and moved in the proximal direction, wherein the proximal side of the needle protection spring supporting surface 12c is moved in the proximal direction by the piston stroke H and abuts against the intermediate bottom 5a of the housing. If, during or shortly before the end of the injection, the user keeps the release button 7 pressed, the holding device 12 nevertheless has an available movement distance W and can travel the desired distance in the proximal direction. The distance or movement distance between the distal end of the button sheath 7c and the gradation 12d of the holding device 12 is dimensioned so that, in the pressed state of the release button 7, the holding device 12 is no longer impeded in its movement in the proximal direction by the release button 7, but a movement distance or distance W remains between the holding device 12 and the button sheath 7c, so that the holding device 12 with its needle protection spring supporting surface 12c can abut against the intermediate bottom 5a, whereby an acoustic and/or tactile signal is generated, which lets the patient know that the injection has been completed and that the injection apparatus can be removed from the injection site. Preferably, the free movement distance or distance W is dimensioned to be greater than or equal to the button stroke H.

Figures 12, 13:
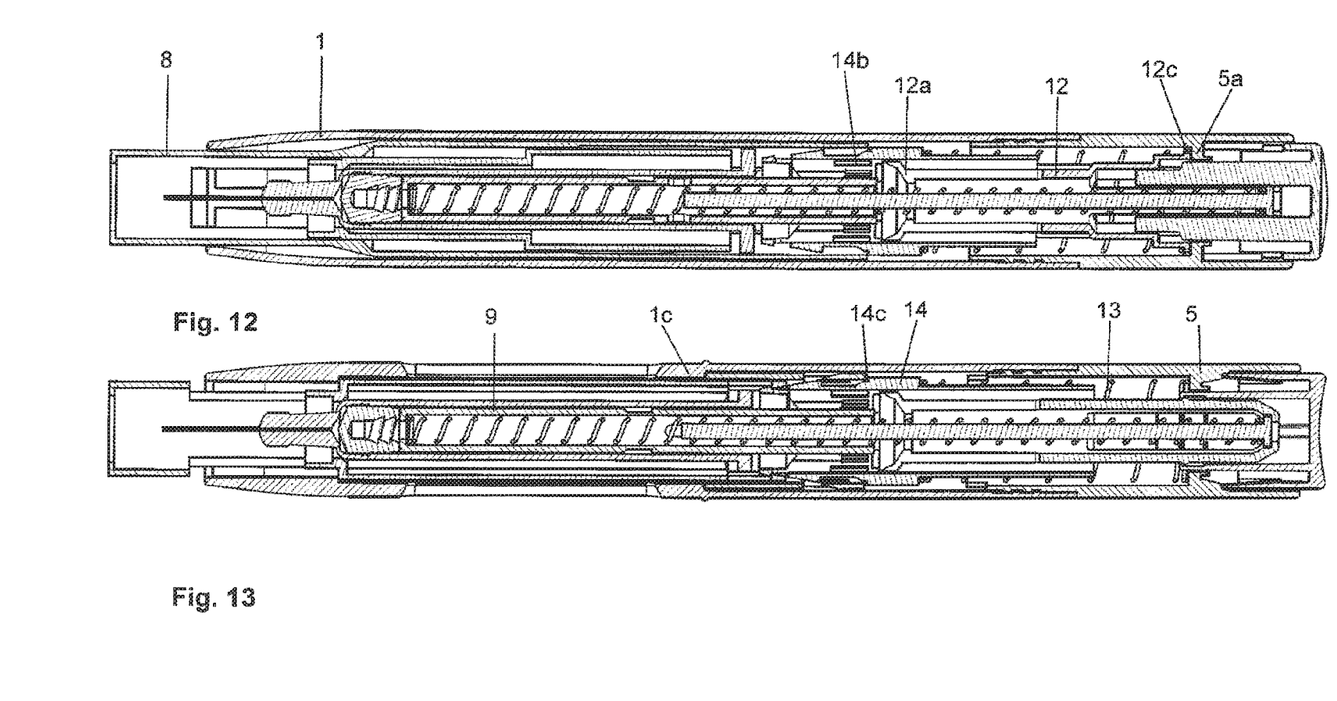

FIGS. 12 and 13:

When the injection device is removed from the injection site, the needle protection spring 13 drives the releasing element 14 in the distal direction, and the releasing element 14 pushes the needle protection sleeve 8, which is also moved in the distal direction, and which protrudes from the distal housing portion 1 in order to cover the needle. Moreover, the blocking means 14b of the releasing element 14 pass by the spring arms 12a of the holding device 12. Then, the proximal ends of the blocking means 14b and the distal surfaces of the spring arms 12a form proximal abutments for the releasing element 14. Thus, the releasing element 14 can no longer be shifted in the proximal direction, and the needle protection sleeve 8 is also blocked for a renewed proximal shifting.

Figure 14:
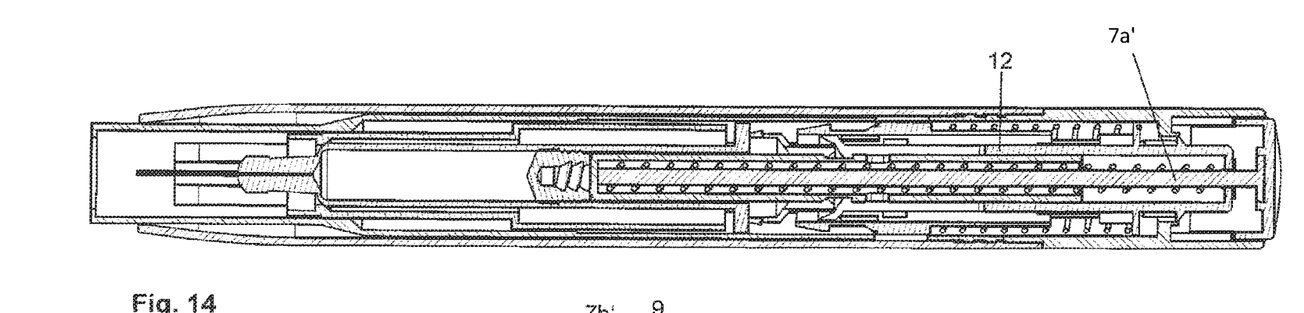
Figure 15:
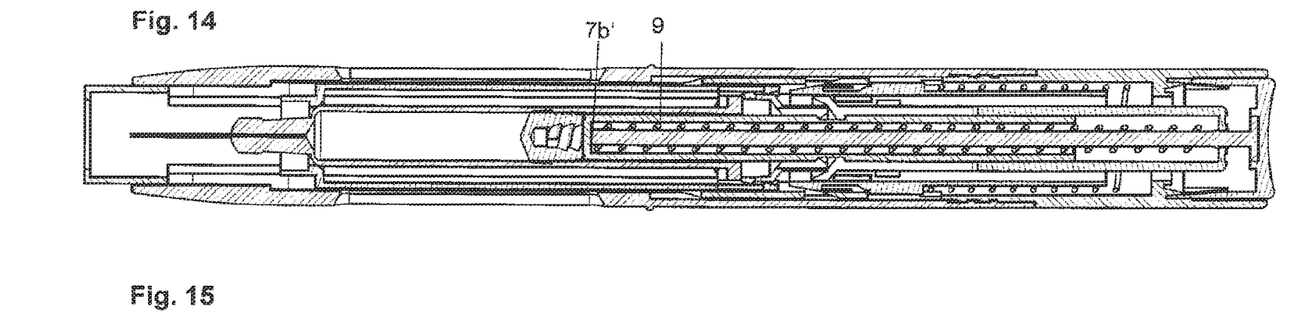

FIGS. 14 and 15:

A second injection device according to the invention comprises the same injection device subsystems as already described in FIGS. 1 to 3, and, in the second embodiment, the release button 7 has an extension arm 7a'. The extension arm 7a' is applied with its distal area, a supporting surface 7b', against the inner distal floor of the piston rod 9. When the user pushes the release button 7 of the injection device and shifts it from a proximal position into a distal position, he shifts the piston rod 9 and thus also the holding device 12 from a first position into a second position in the distal direction. The subsequent steps such as, for example, the release, occur in the same way as described in the preceding embodiment.

Figure 16:
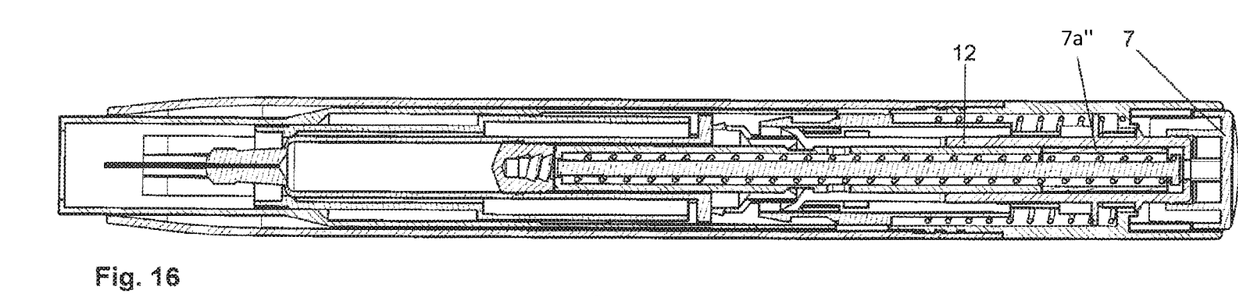
Figure 17:
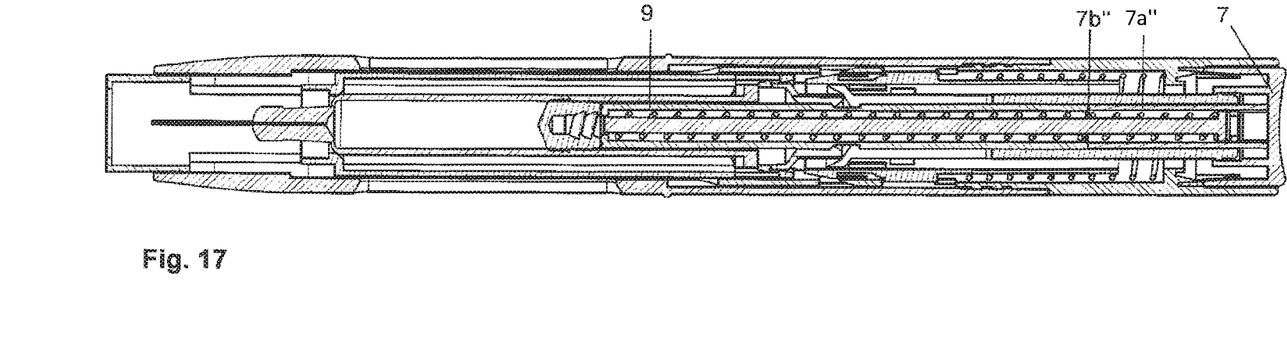

FIGS. 16 and 17:

An additional injection device according to the invention also comprises the same injection device subsystems as already described in FIGS. 1 to 3. In this embodiment, the release button 7 comprises an extension sleeve 7a" attached on the inner side, wherein the extension sleeve 7a" abuts with its supporting surface 7b" against the proximal area of the piston rod 9, and wherein, upon releasing the injection device or pressing the release button 7 from a proximal position into a distal position, the piston rod 9 with the holding device 12 is also shifted in the distal direction from a first position into a second position. The other releasing steps follow as already described.

What is claimed is:

1. An injection device for injecting medicaments, comprising:
   a housing;
   a needle protection sleeve, a portion of which is configured to protrude from a distal end of the housing;
   a needle protection spring configured to move the needle protection sleeve from a proximal position into a distal position;
   a syringe device comprising a syringe holder, which is axially moveable in the needle protection sleeve, a syringe comprising a piston, a medicament and a needle on a distal end of the syringe device, wherein the syringe is placed in the syringe holder of the syringe device;
   a holding device;
   a releasing element surrounding the holding device and in contact with the needle protection spring;
   a drive device configured to be axially moveable in the housing and to be uncoupled from the holding device, wherein the drive device stores energy for moving the syringe holder in a distal direction and for discharging the medicament by advancing the piston in the distal direction in the syringe; and a release button assembly comprising a release button for enabling the drive device to be uncoupled from the holding device, wherein the release button is operatively connected to the drive device and to the holding device, such that a distal movement of the release button causes the drive device to move distally whereby the holding device is shifted by the drive device in the distal direction.

2. The injection device of claim 1, wherein the drive device comprises a piston rod and a drive spring, wherein the drive spring is configured to move the piston rod such that the drive spring first moves the syringe holder via the piston rod in the distal direction, and then moves the piston via the piston rod for discharging the medicament.

3. The injection device of claim 2, wherein before releasing the injection device, the release button is operatively connected to the piston rod by a connecting element such that a distal movement of the release button moves the piston rod in the distal direction.

4. The injection device of claim 2, wherein the drive spring is arranged between a distal wall of the piston rod and a proximal end of the holding device.

5. The injection device of claim 2, wherein the holding device comprises spring arms, and the piston rod comprises a groove on its outer surface into which the spring arms are configured to detachably engage.

6. The injection device of claim 5, wherein the release button assembly comprises a supporting surface operatively coupled to the piston rod such that in response to a shifting of the release button from a proximal position into a distal position, the piston rod shifts from a first position into a second position, and the holding device is shifted in the distal direction by the spring arms of the holding device, which engage in the groove of the piston rod.

7. The injection device of claim 5, wherein the piston rod is held against a force of the drive spring by the spring arms of the holding device being in a detachable engagement with the groove of the piston rod, and wherein the releasing element surrounds the spring arms and prevents the spring arms from opening.

8. The injection device of claim 7, wherein the needle protection spring is arranged between the releasing element and the holding device.

9. The injection device of claim 7, wherein the needle protection sleeve and the releasing element can be shifted together in the proximal direction with respect to the holding device when the needle protection sleeve is pushed against an injection site, and wherein, for releasing the drive device, the holding device and the releasing element move towards one another in order to release the spring arms of the holding device from the groove of the piston rod such that the piston rod can be moved via the force of the drive spring in the distal direction to first advance the syringe holder and then the piston in the distal direction.

10. The injection device of claim 7, wherein once the distal area of the needle protection sleeve is removed from the injection site, the needle protection sleeve and the releasing element can be moved by the force of the needle protection spring in relation to the housing and to the holding device in the distal direction.

11. The injection device of claim 7, wherein the releasing element comprises blocking means, such that, after the needle protection sleeve and the releasing element have moved in the distal direction, another proximal movement of the needle protection sleeve can be prevented.

12. The injection device according to claim 5, wherein the holding device is configured such that it can be moved by the needle protection spring and/or the drive spring in the proximal direction once a proximal end of the piston rod has moved in a distal direction past the spring arms of the holding device such that the spring arms are moved radially inward.

13. The injection device according to claim 5, wherein the holding device is configured to be movable by the needle protection spring and/or the drive spring in the proximal direction once a proximal end of the piston rod has moved in a distal direction past the spring arms of the holding device such that a proximal area of the holding device abuts against a proximal housing portion of the housing and causes an acoustic and/or tactile signal to be generated.

14. The injection device of claim 1, wherein the holding device and the release button are movable relative to one another by a free movement distance such that when the holding device is released, the holding device can be moved in the proximal direction over the movement distance.

15. An injection device for injecting a medicament, comprising:
a housing;
a needle protection sleeve axially movable relative to the housing and configured to extend past a distal end of the housing when moved into a distal position by a needle protection spring;
a syringe holder axially moveable in the needle protection sleeve, the syringe holder configured to hold a syringe comprising a piston;
a drive device comprising a piston rod and a drive spring, the drive device configured to be axially moveable in the housing, wherein the drive spring stores energy for moving the syringe holder in the distal direction and for discharging the medicament to be injected;
a holding device configured to be releasably coupled with the drive device;
and
a release button for enabling the drive device to be uncoupled from the holding device,
wherein a distal movement of the release button causes the piston rod to move distally and to drive the holding device in the distal direction.

16. The injection device of claim 15, wherein the holding device comprises spring arms, and the piston rod comprises a groove on its outer surface into which the spring arms are configured to detachably engage.

17. The injection device of claim 16, wherein in response to a shifting of the release button from a proximal position into a distal position, the piston rod shifts from a first position into a second position, and the holding device is shifted in the distal direction by the spring arms of the holding device being detachably engaged in the groove of the piston rod.

18. The injection device according to claim 16, wherein the holding device is configured to be movable by the needle protection spring and/or the drive spring in the proximal direction once a proximal end of the piston rod has moved in a distal direction past the spring arms of the holding device such that a proximal area of the holding device abuts against a proximal housing portion of the housing and causes an acoustic and/or tactile signal to be generated.

19. The injection device of claim 16, wherein the piston rod is held against a force of the drive spring by the spring arms of the holding device being in a detachable engagement with the groove of the piston rod, and wherein a releasing element surrounds the spring arms and prevents the spring arms from opening, the releasing element being in contact with the needle protection spring.

20. The injection device of claim 19, wherein for releasing the drive device, the holding device and the releasing element move in opposite directions to thereby release the detachable engagement between the spring arms of the holding device and the groove of the piston rod such that the piston rod can be moved via the force of the drive spring in the distal direction to first move the syringe holder and then discharge the medicament to be injected.

21. The injection device of claim 15, wherein the release button comprises extension arms with supporting surfaces that reach, when the release button is pushed from a proximal position into a distal position, a proximal area of the piston rod to shift the piston rod.

* * * * *